(12) United States Patent
Bauhahn et al.

(10) Patent No.: US 7,066,910 B2
(45) Date of Patent: Jun. 27, 2006

(54) PATIENT DIRECTED THERAPY MANAGEMENT

(75) Inventors: Ruth Elinor Bauhahn, Fridley, MN (US); John W. Forsberg, St. Paul, MN (US); Steven James Nelson, Wyoming, MN (US); Kenneth Timothy Heruth, Edina, MN (US)

(73) Assignee: Medtronic, Inc., Minneapolis, MN (US)

(*) Notice: Subject to any disclaimer, the term of this patent is extended or adjusted under 35 U.S.C. 154(b) by 299 days.

(21) Appl. No.: 09/982,763

(22) Filed: Oct. 18, 2001

(65) Prior Publication Data

US 2003/0036783 A1    Feb. 20, 2003

Related U.S. Application Data

(63) Continuation-in-part of application No. 09/560,064, filed on Apr. 27, 2000.

(51) Int. Cl.
*A61M 1/00* (2006.01)

(52) U.S. Cl. .................................. 604/151; 604/891.1

(58) Field of Classification Search ................. 607/60, 607/59, 63; 604/65–67, 131, 151–154, 891.1; 128/903
See application file for complete search history.

(56) References Cited

U.S. PATENT DOCUMENTS

| | | | |
|---|---|---|---|
| 4,126,139 A | 11/1978 | Walters | |
| 4,236,524 A | 12/1980 | Powell | |
| 4,273,133 A | 6/1981 | Hartlaub | |
| 4,282,872 A * | 8/1981 | Franetzki et al. | ............. 604/67 |
| 4,304,238 A | 12/1981 | Fischer | |
| 4,365,633 A | 12/1982 | Loughman | |
| 4,373,527 A | 2/1983 | Fischell | |
| 4,388,927 A | 6/1983 | Schober | |
| 4,390,023 A | 6/1983 | Rise | |
| 4,398,537 A | 8/1983 | Holmbo | |
| 4,407,288 A | 10/1983 | Langer et al. | |
| 4,424,812 A | 1/1984 | Lesnick | |
| 4,459,989 A | 7/1984 | Borkan | |
| 4,467,810 A | 8/1984 | Vollmann | |
| 4,469,481 A * | 9/1984 | Kobayashi | ................... 604/67 |
| 4,485,818 A | 12/1984 | Leckrone | |
| 4,525,165 A | 6/1985 | Fischell | |
| 4,562,841 A | 1/1986 | Brockway | |
| 4,573,994 A | 3/1986 | Fischell | |
| 4,612,934 A | 9/1986 | Borkan | |
| 4,619,653 A | 10/1986 | Fischell | |
| 4,690,144 A | 9/1987 | Rise | |
| 4,731,051 A | 3/1988 | Fischell | |
| 4,793,353 A | 12/1988 | Borkan | |

(Continued)

FOREIGN PATENT DOCUMENTS

EP    0 811 395 A2    12/1997

(Continued)

OTHER PUBLICATIONS

PCT International Search Report, 8 pages.

*Primary Examiner*—Mark Bockelman
(74) *Attorney, Agent, or Firm*—Banner & Witcoff, Ltd.

(57) ABSTRACT

An method and system that allows a patient to access stored preset patient therapy programs, that are resident in a medical device such an implantable pump or a combination medical device having an implantable pump and a implantable neural stimulator, and to create personalized therapy programs or automatic timing therapy programs from preset therapy programs to accommodate the patient's particular activity. Alternatively, the patient can select and access stored preset patient therapy programs and combine at least two modified or unmodified preset therapy programs to create personalized therapy programs.

11 Claims, 13 Drawing Sheets

U.S. PATENT DOCUMENTS

| | | | |
|---|---|---|---|
| 4,846,180 A | 7/1989 | Buffet | |
| 4,958,632 A | 9/1990 | Duggan | |
| 5,159,926 A | 11/1992 | Ljungstroem | |
| 5,285,781 A | 2/1994 | Brodard | |
| 5,292,341 A | 3/1994 | Snell | |
| 5,318,593 A | 6/1994 | Duggan | |
| 5,360,437 A | 11/1994 | Thompson | |
| 5,370,672 A | 12/1994 | Fowler et al. | |
| 5,443,486 A | 8/1995 | Hrdlicka | |
| 5,456,691 A * | 10/1995 | Snell | 607/30 |
| 5,456,692 A | 10/1995 | Smith | |
| 5,545,186 A | 8/1996 | Olson | |
| 5,601,617 A | 2/1997 | Loeb | |
| 5,626,629 A | 5/1997 | Faltys | |
| 5,681,285 A * | 10/1997 | Ford et al. | 604/151 |
| 5,697,960 A | 12/1997 | Molin | |
| 5,716,382 A | 2/1998 | Snell | |
| 5,755,736 A | 5/1998 | Gillberg | |
| 5,855,593 A | 1/1999 | Olson | |
| 5,893,883 A | 4/1999 | Torgerson | |
| 5,938,690 A | 8/1999 | Law et al. | |
| 5,991,656 A | 11/1999 | Olson | |
| 6,044,301 A | 3/2000 | Hartlaub | |
| 6,052,614 A | 4/2000 | Morris | |
| 6,052,620 A | 4/2000 | Gillberg | |
| 6,052,624 A | 4/2000 | Mann | |
| 6,058,326 A | 5/2000 | Hess | |
| 6,061,596 A | 5/2000 | Richmond | |
| 6,099,479 A | 8/2000 | Christopherson | |
| 6,141,581 A | 10/2000 | Olson | |
| 6,169,924 B1 | 1/2001 | Meloy | |
| 6,178,350 B1 | 1/2001 | Olson | |
| 6,181,969 B1 | 1/2001 | Gord | |
| 6,208,894 B1 | 3/2001 | Schulman | |
| 6,249,703 B1 | 6/2001 | Stanton | |
| 6,259,947 B1 | 7/2001 | Olson | |
| 6,289,247 B1 | 9/2001 | Faltys | |
| 6,308,102 B1 | 10/2001 | Sieracki et al. | |
| 6,354,299 B1 | 3/2002 | Fischell et al. | |
| 6,381,496 B1 | 4/2002 | Meadows et al. | |
| 6,393,325 B1 | 5/2002 | Mann et al. | |
| 6,516,227 B1 | 2/2003 | Meadows | |
| 6,587,724 B1 | 7/2003 | Mann | |

FOREIGN PATENT DOCUMENTS

| | | |
|---|---|---|
| EP | 1134003 | 9/2001 |
| EP | 0939661 | 8/2002 |
| GB | 2069844 | 9/1981 |
| WO | WO 84/03218 | 8/1984 |
| WO | WO 95/13112 | 5/1995 |
| WO | WO 96/01665 | 1/1996 |
| WO | WO 96/30081 | 10/1996 |
| WO | WO 97/43002 | 11/1997 |
| WO | WO 01/39831 A1 | 6/2001 |
| WO | 0152935 | 7/2001 |
| WO | WO 01/93952 A1 | 12/2001 |
| WO | WO 01/93953 | 12/2001 |

* cited by examiner

INS ENVIRONMENT

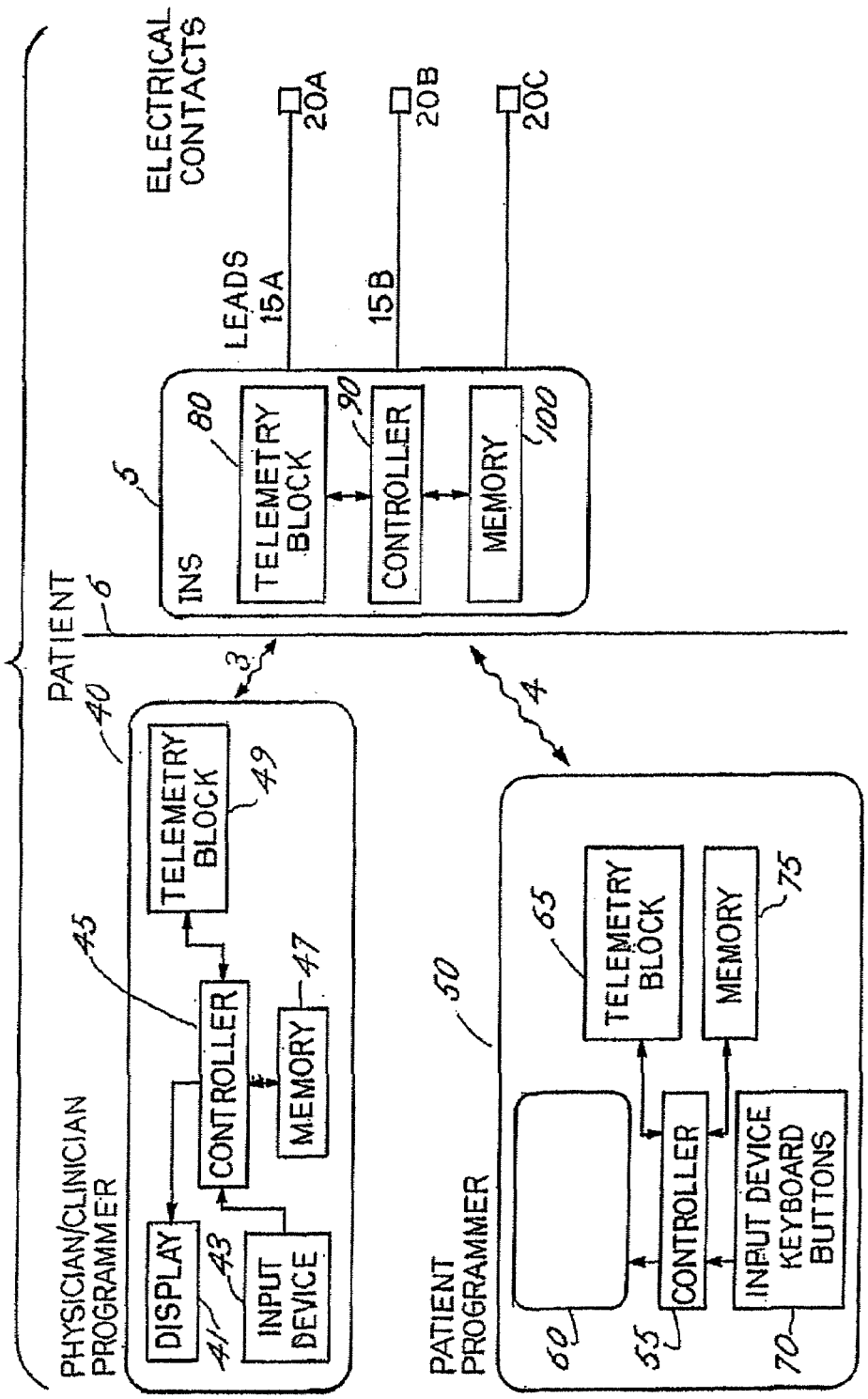

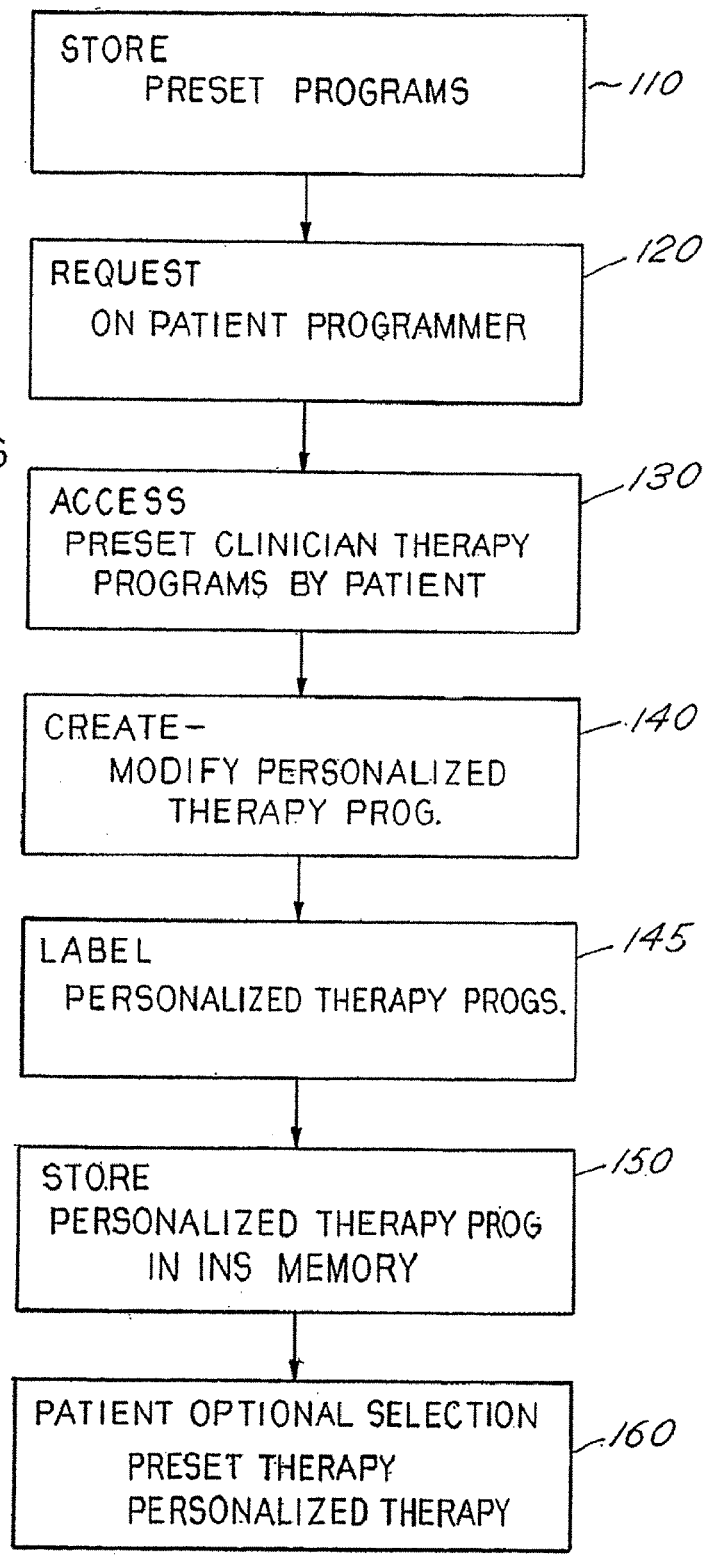

PATIENT DIRECTED THERAPY MANAGEMENT

This is a continuation-in-part application of U.S. patent application Ser. No. 09/560,064, filed Apr. 27, 2000, for which priority is claimed.

FIELD OF THE INVENTION

The present invention relates generally to medical implantable devices. More particularly, the invention relates to a method and system for patient directed therapy management of implantable medical devices used to influence the human body.

BACKGROUND OF THE INVENTION

The medical device industry produces a wide variety of electronic and mechanical devices for treating patient medical conditions. Depending upon the medical condition, medical devices can be surgically implanted or connected externally to the patient receiving treatment. Clinicians use medical devices alone, or in combination with other medical devices, drug therapies, and surgery to treat patient medical conditions. For some medical conditions, medical devices provide the best, and sometimes the only, therapy to restore an individual to a more healthful condition and a fuller life.

Implantable medical devices are commonly used today to treat patients suffering from various ailments. Implantable medical devices can be used to treat any number of conditions such as pain, incontinence, movement disorders such as epilepsy and Parkinson's disease, and sleep apnea. Additionally, use of implantable medical devices appears promising to treat a variety of physiological, psychological, and emotional conditions.

One type of implantable medical device is an Implantable Neuro Stimulator (INS). The INS is implanted at a predetermined location in the patient's body. The INS generates and delivers mild electrical impulses to neurostimulation areas in the body using an electrical lead. The INS electrical stimulation signals at neurostimulation sites or areas influence desired neural tissue, tissue areas, nervous system and organs to treat the ailment of concern. The stimulation sites can also include the spinal cord, brain, body muscles, peripheral nerves or any other site selected by a physician. For example, in the case of pain, electrical impulses may be directed to cover the specific sites where the patient is feeling pain. Neurostimulation can give patients effective pain relief and can reduce or eliminate the need for repeat surgeries and the need for pain medications.

In the case to an INS, the system generally includes an implantable neuro stimulator (INS) (also known as an implantable pulse generator (IPG)), an external physician or clinician programmer, a patient programmer and at least one electrical lead. An INS is typically implanted near the abdomen of the patient, or other stimulation area as required. The lead is a small medical wire with special insulation and contains a set of electrodes small electrical contacts) through which electrical stimulation is delivered. The INS can be powered by an internal source such as a rechargeable or non-rechargeable battery or by an external source such as a radio frequency transmitter. The INS contains electronics to generate and send precise. electrical pulses to the stimulation area to provide the desired treatment therapy. The clinician programmer is an external device that allows the physician or clinician to create and store preset stimulation therapy to be delivered by the INS. The clinician programmer communicates with the INS using radio waves, for example via telemetry. The patient programmer is an external hand-held device that allows the patient to optimize the stimulation therapy delivered by the INS. The patient programmer also communicates with the INS using radio waves, such as telemetry.

Another type of implantable medical device is an implantable drug infusion pump. The drug infusion pump is implanted at a predetermined location in the patient's body. Typically, the implantable drug infusion pump outlet is connected to the proximal end of an infusion catheter. The catheter is a flexible tube with a lumen typically running the length of the catheter. The distal end of the catheter is positioned to infuse a drug or drug combination to target sites in a patient's body. Target sites in a patient's body include but are not limited to an internal cavity, a blood vessel, any organ, other tissue or fluid in the body The drug or other therapeutic substance flows from the pump through the lumen in the catheter at a programmed rate. The drug or drug combination is intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like.

In the case of the implantable drug infusion pump, the system generally includes an implantable drug infusion pump, an external physician or clinician programmer, a patient programmer, and an infusion catheter. The implantable drug infusion pump contains a power source and electronics that allow the correct flow of therapeutic to be delivered to the treatment area. The physician or clinician programmer is used to create and store preset infusion therapies to be delivered by the implantable drug infusion pump. The clinician programmer communicates with the implantable drug infusion pump using radio waves, for example via telemetry. The patient programmer is an external hand-held device that allows the patient to optimize the stimulation therapy delivered by the implantable drug infusion pump. The patient programmer also communicates with the implantable drug infusion pump using telemetry.

A third type of implantable medical device is a combination medical device. Both the INS and the implantable drug infusion pump may also be used in combination to provide a more effective therapy. In some applications, the efficacy of treatment may be enhanced if tissue-requiring treatment is stimulated while drugs are being administered. Additionally, one system could be used as a base treatment system with the other providing additional treatment if the base system cannot provide an adequate response. In such a system, the combination devices could be separately housed devices or devices that share a common housing. The system may include both an INS and an implantable drug infusion pump along with a common infusion catheter that contains both a lumen and electrodes to provide the treatment.

In the above devices or combination devices, a clinician typically creates and stores preset patient therapy programs that are executed by the devices to deliver therapy to the patient. The preset patient therapy programs include specific therapy parameters that are set and created by clinicians based on industry or clinician preferences, patient feedback, a patient's test results, or a combination of all of the above. The patient therapy programs are then downloaded into the devices memory using the clinician programmer. The patient therapy programs then reside in both clinician programmer memory and the devices memory. The stored preset patient therapy programs, which include specific therapy parameters, will allow the devices to generate the appropriate electrical stimulation signals or drug infusion flows for the patient's specific needs. The stored patient therapy programs may contain parameters, which include for example, electrode settings, signal intensity or strength (amplitude), signal duration (pulse width), signal timing and cycling (pulse frequency or rate), drug infusion volume, start time, and stop time.

At present, patients do not have the ability to select and assemble the preset therapy programs, which were created by the clinician, or to create his/her own personalized therapy programs. A patient can typically access the stored preset clinician therapy programs but cannot create personalized therapy programs himself/herself. A patient must use and live with the preset therapy programs that have been created by the clinician. Moreover, the targeted treatment areas by the implantable medical devices are usually situated to alleviate or address pain or discomfort due to one body position or activity, e.g., sitting compared to walking, jogging or running. As a result, the combination of specifically situated stimulation and/or infusion areas and unchangeable clinician created preset therapy programs can lead to discomfort or reduced therapy when a patient engages in activities that were not accounted for or foreseen by the clinician. The inability to modify the stored therapy programs can thus limit the activities that a patient may wish to engage in.

For the foregoing reasons there is a need for a method and system that will allow patients to access stored preset clinician therapy programs so that the patient can create new personalized therapy programs that will enable the patient to participate in a variety of activities without undue discomfort or the need to visit a clinician for additional preset therapy programs.

It is an objective of the present invention to provide a method and system to give patients the ability to assemble, label and store their own personalized therapy programs, on demand, from among the preset clinician therapy programs that are resident in device's memory.

It is an objective of the present invention to provide a method and system to give patients more control to create personalized therapy programs and settings to fit their unique lifestyles thereby increasing patient satisfaction.

SUMMARY OF THE INVENTION

The present invention provides a method and system that allows a patient to select and access stored patient therapy programs, that are resident in the INS device, and modify the stored therapy programs to accommodate his/her particular lifestyle, thereby creating and storing personalized therapy programs. The patient can select and access stored patient therapy programs and combine in an unmodified manner at least two of the accessed therapy programs to create personalized therapy programs. The present invention also gives the patient the ability to select and access stored patient therapy programs, to modify the accessed preset therapy programs and then combine the modified preset therapy programs to create personalized therapy programs.

In accordance with the present invention, there is provided a method for patient directed therapy management in an implantable drug infusion pump. The method comprised of: accessing at least one preset clinician drug therapy program stored in the drug delivery pump; creating at least one personalized drug therapy program from the accessed preset clinician drug therapy program; and executing at least one personalized drug therapy program for the drug delivery pump.

In accordance with the present invention, there is provided a system for patient directed therapy management that allows a patient to select and access stored patient therapy programs that are resident in the combination device and to modify the stored therapy programs to create and store personalized therapy programs that accommodate the patient's particular lifestyle. The system is comprised of a first medical device comprising a first telemetry block and a first memory with at least one preset clinician therapy program; a second medical device comprising a second telemetry block and a second memory with at least one preset clinician therapy program; and a patient programmer comprising a third telemetry block, the patient programmer configured to allow creation of at least one personalized therapy program for the first medical device, the patient programmer able to store and execute the personalized therapy program.

It is contemplated that the combined medical device comprise any medical device using preset therapy programs, including, but not limited to, pacemakers, defibrillators, cochlear implants, implantable diagnostic devices for detecting bodily conditions of certain organs, like the brain or the heart, and drug delivery systems having an implantable pump.

BRIEF DESCRIPTION OF THE DRAWINGS

FIG. 3 is a schematic block diagram of an INS in accordance with an embodiment of the present invention.

FIG. 4 depicts a block diagram that shows a method of the present invention to create personalized therapy programs.

DESCRIPTION OF THE PREFERRED EMBODIMENTS

The present invention is a method and system that allows a patient to select and access stored preset clinician therapy programs from a medical device or a combination medical device memory and to modify the preset clinician therapy programs to create and store personalized therapy programs through the use of a patient programmer. The present invention gives the patient the ability to configure personalized therapy programs that accommodate the patient's particular needs, lifestyle, and desires from combined and/or modified stored preset clinician therapy programs.

One skilled in the art will recognize that the method and system for patient directed therapy management of the present invention can be used with any number of medical devices requiring the use of preset therapy programs, including, but not limited to pacemakers, defibrillators, cochlear implants, neuro stimulators and drug delivery pumps. In addition, the method and system for patient directed therapy management may also be used with a combination device comprising two or more devices from the above list. The following embodiments will describe the invention with the use of a neuro stimulator, an implantable drug infusion pump, and a combination device comprising a neuro stimulator and an implantable drug pump. It should be recognized by one skilled in the art that the arrangements and configurations of the present invention may be altered without departing from the true spirit and scope of the invention.

Figure 1:
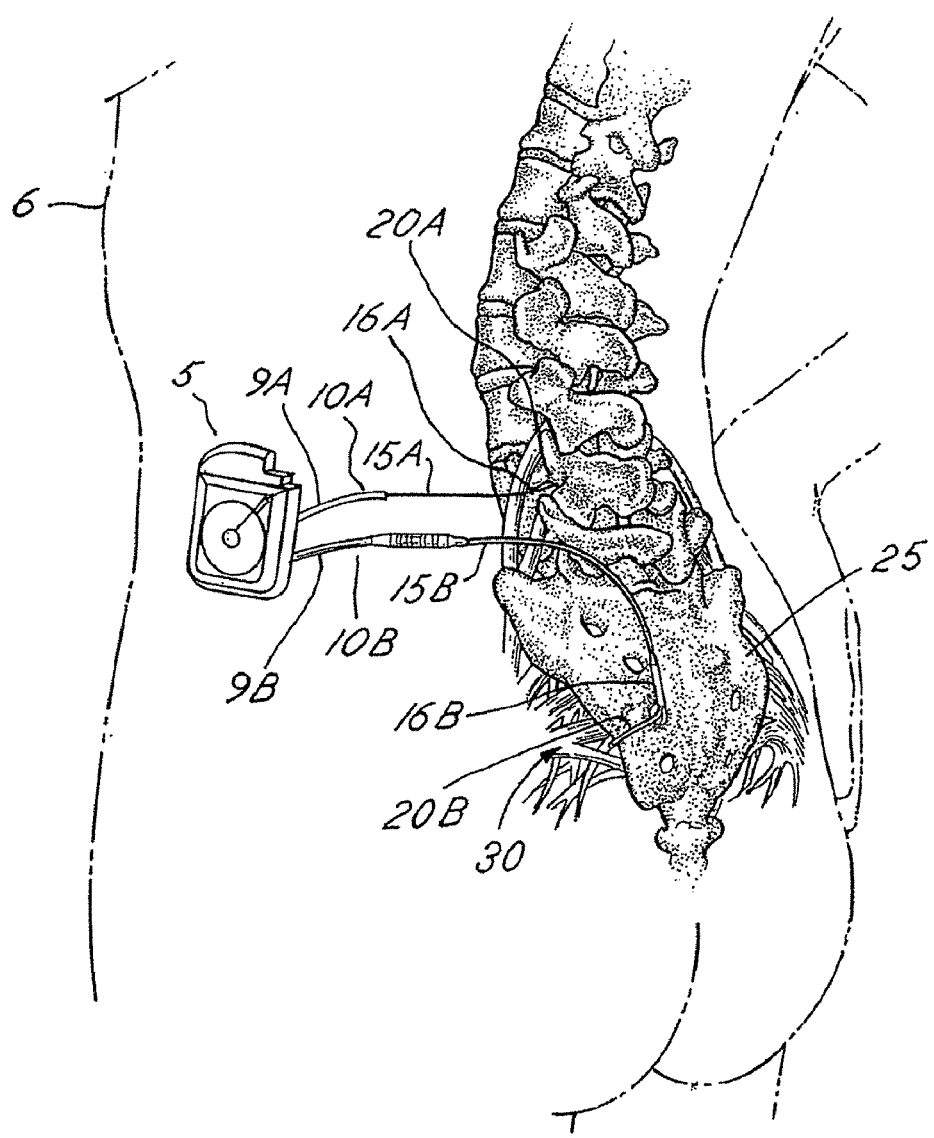
FIG. 1 illustrates an implantable medical device as could be implanted in a human body to deliver stimulation therapy.

FIG. 1 shows a general environment of an Implantable Neuro Stimulator (INS) 5 medical device in a patient 6 including leads 15A and 15B, and lead extensions 10A and 10B. The INS 5 is preferably a modified implantable pulse generator that will be available from Medtronic, Inc. with provisions for multiple pulses occurring either simultaneously or with one pulse shifted in time with respect to the other, and having independently varying amplitudes, pulse widths and directional sequence. The INS 5 contains a power source and electronics to send precise, electrical pulses to the spinal cord, brain, or neural tissue to provide the desired treatment therapy. The INS 5 can be powered by an internal source such as a rechargeable or non-rechargeable battery or by an external source such as a radio frequency transmitter. In an embodiment of the present invention, the INS 5 provides electrical stimulation by way of pulses, however other forms of stimulation may be used such as continuous electrical stimulation, magnetic pulses, or continuous magnetic stimulation.

The INS 5 can use one or more leads 15A and 15B and extensions 10A and 10B for delivering therapy. The leads 15A and 15B, which are surgically implanted, are comprised of one or more insulated electrical conductors with a connector on the proximal end 9A and 9B and electrical contacts or electrodes 20A and 20B on the distal end 16A and 16B. A lead 15A and 15B is a small medical wire with special insulation. Those skilled in the art will appreciate that any variety of leads may be used to practice the present invention.

As shown in FIG. 1, the leads 15A and 15B are implanted and positioned to stimulate a specific site or area. Alternatively, the leads 15A and 15B may be positioned along a peripheral nerve, adjacent neural tissue, positioned to stimulate muscle tissue or other stimulation site chosen by a clinician. The leads 15A and 15B contain one or more electrodes (small electrical contacts) through which electrical stimulation is delivered from the INS 5 to the targeted neural tissue. The electrodes 20A and 20B may be arranged in a predetermined physical layout. For example, where there is more than one electrode 20A and 20B, the electrodes may be arranged in a linear array, in multiple linear arrays, or in a particular geometric array such as a triangle, square, rectangle, circle, etc. In addition, the INS 5 may deliver stimulation therapy signals via the electrodes in a predetermined directional sequence based on the electrode's physical layout in the stimulation area.

Figure 2A:
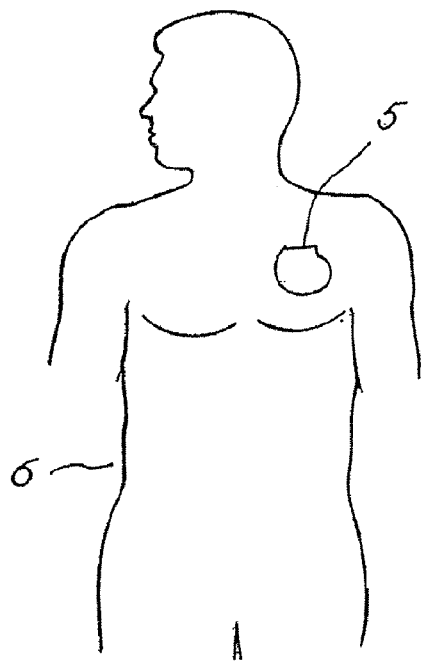
FIGS. 2A–D illustrate locations where the implantable medical device can be implanted in the human body other than the location shown in FIG. 1.
Figure 2B:
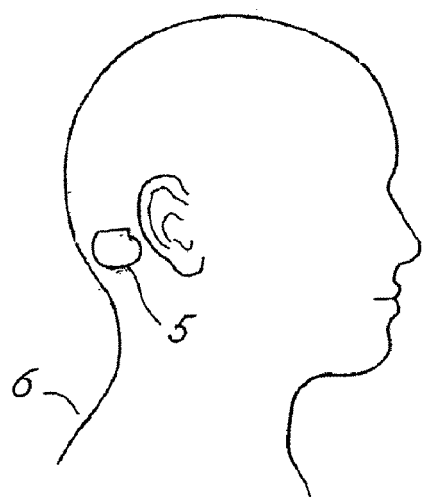
Figure 2C:
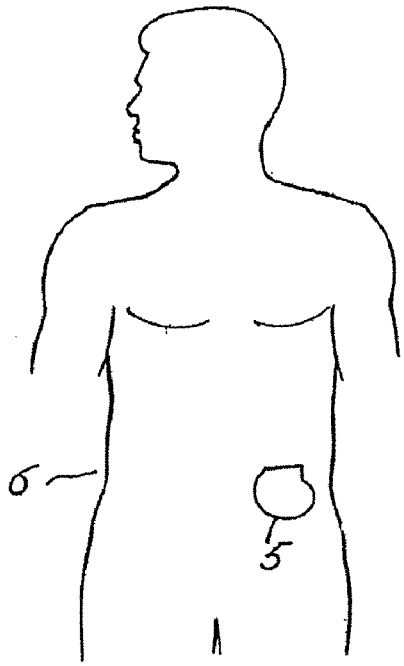
Figure 2D:
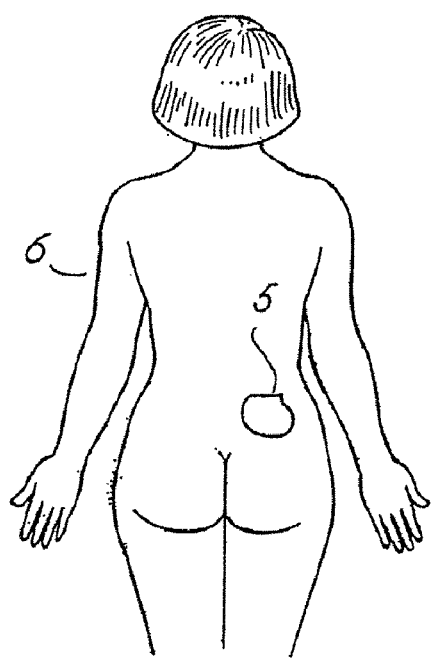

FIGS. 2A–D generally illustrate locations where the INS can be implanted in the human body other than the location shown in FIG. 1, i.e., within the lower left abdominal region of the patient 6 illustrated in FIG. 2C. Other preferred embodiments for the placement of INS 5 within a human patient are further shown in FIGS. 2A, 2B, and 2D. As shown in FIG. 2A, the INS 5 can be implanted in a pectoral region of the patient. As shown in FIG. 2B, the INS 5 can be implanted in a region behind the ear of a patient 6, and more specifically in the mastoid region. As shown in FIG. 2D, the INS 5 can be placed in the lower back or upper buttock region of the patient 6.

Figure 6:
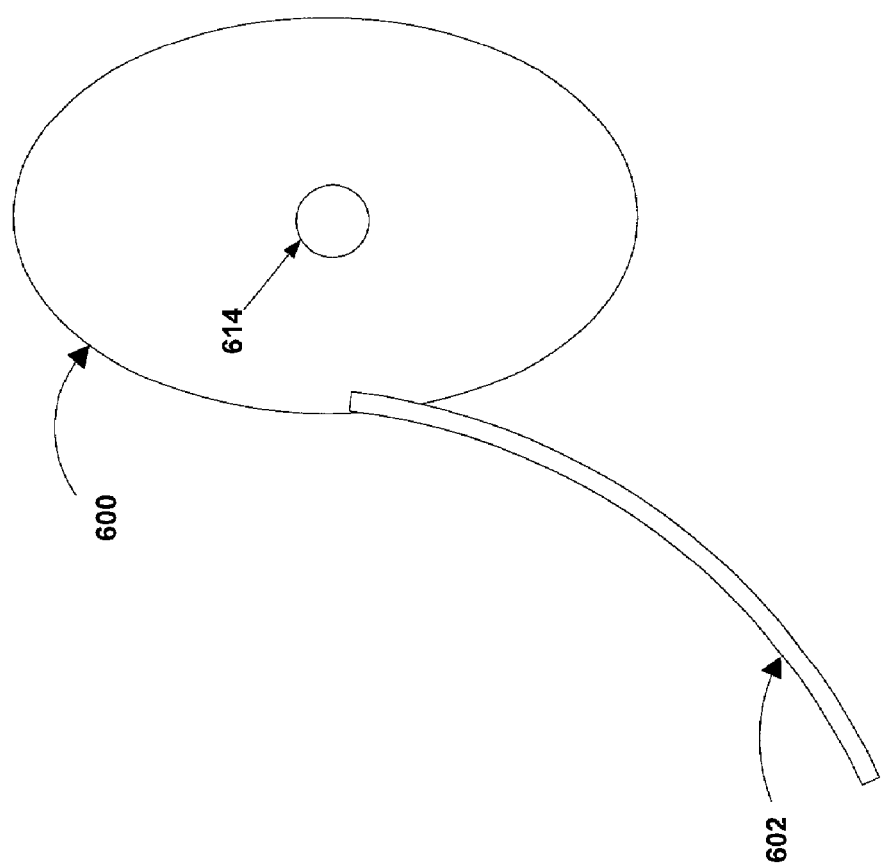
FIG. 6 illustrates an implantable drug infusion device that could be implanted in a human body to deliver drug infusion therapy.

FIG. 6 shows the general environment of an implantable drug infusion pump 600 and an infusion catheter 602. The system distributes a therapeutic drug or agent to sites a physician selects for treatment. The system uses a pump 600 that can be an implantable pump like the Medtronic SynchroMed® pump as described by Medtronic brochure entitled "SynchroMed® Infusion System." As depicted in the figure, the pump 600 has a port 614 into which a hypodermic needle can be inserted to inject a therapeutic to fill the pump 600. As an alternative, the pump 600 may contain a reservoir, not shown, having a predetermined volume of therapeutic that is pumped at a predetermined rate. The implantable drug infusion pump 600 contains a power source and electronics to deliver the therapeutic drug or agent to the selected treatment sites.

The implantable drug infusion pump outlet is connected to the proximal end of an infusion catheter 602. The infusion catheter 602 is a flexible tube with a lumen typically running the length of the catheter. The distal end of the infusion catheter 602 is positioned to infuse a drug or agent to target sites in a patient's body. Target sites in the body include but are not limited to an internal cavity, a blood vessel, any organ, other tissue or fluid in the body. The drug or agent flows from the pump 600 through the lumen in the catheter 602 at a programmed rate. The drug or agent is intended to have a therapeutic effect. Such drugs or agents may include pharmaceutical compositions, genetic materials, biologics, and other substances. Pharmaceutical compositions are chemical formulations intended to have a therapeutic effect such as intrathecal antispasmodics, pain medications, chemotherapeutic agents, and the like.

Figure 10:
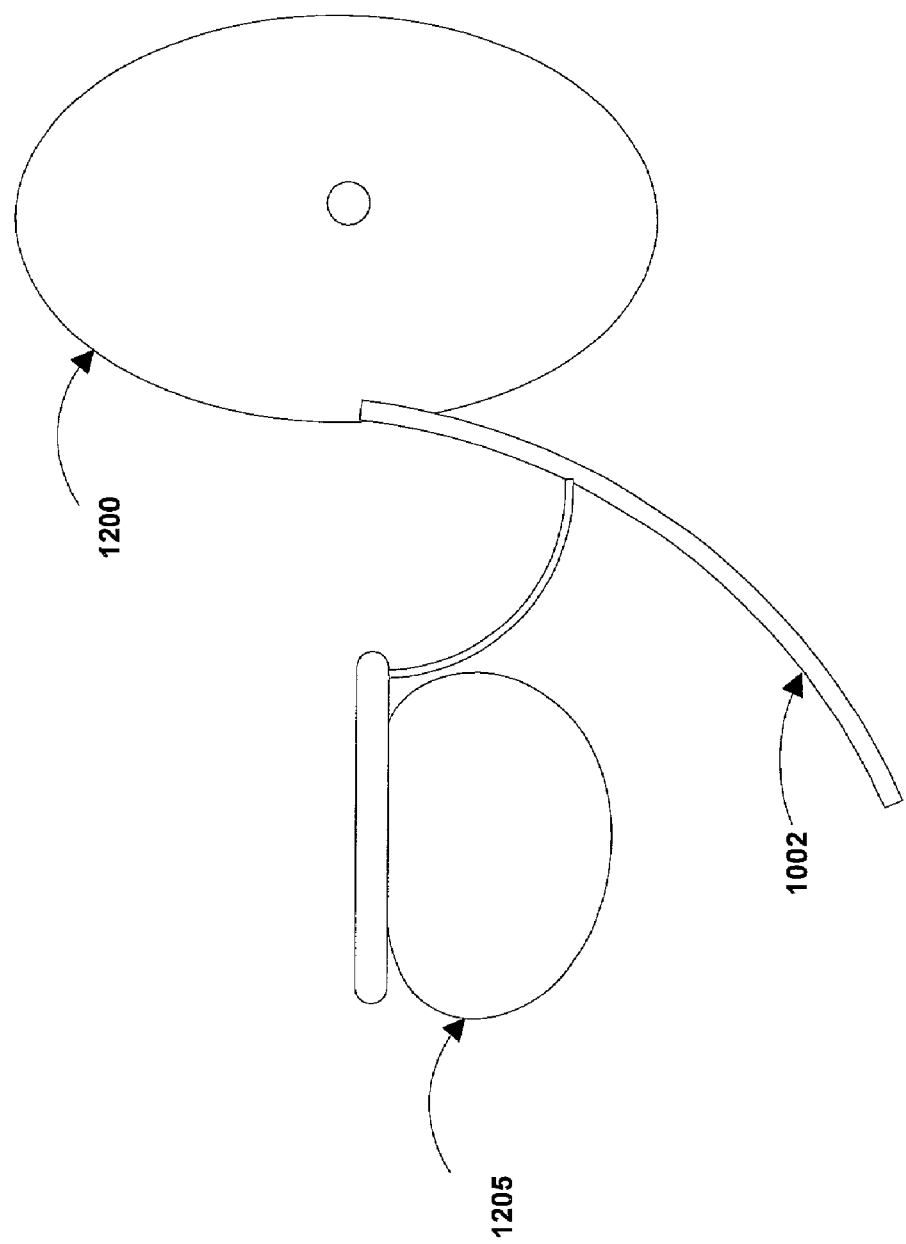
FIG. 10 illustrates a combination device consisting of an implantable drug infusion pump and a neuro stimulator that could be implanted in a human body to deliver a combination drug and stimulation therapy.

FIG. 10 shows the general environment of a combination device that includes an implantable drug infusion pump 1200 and an INS 1205. The combination illustrated in FIG. 10 depicts the devices as being two separate devices for simplicity, but one skilled in the art will recognize that both devices may be combined into one housing and perform the same or similar functions. Similarly, one skilled in the art will recognize that the combination device may include different combinations of devices that include, but are not limited to, pacemakers, defibrillators, and/or cochlear implants.

Figure 11:
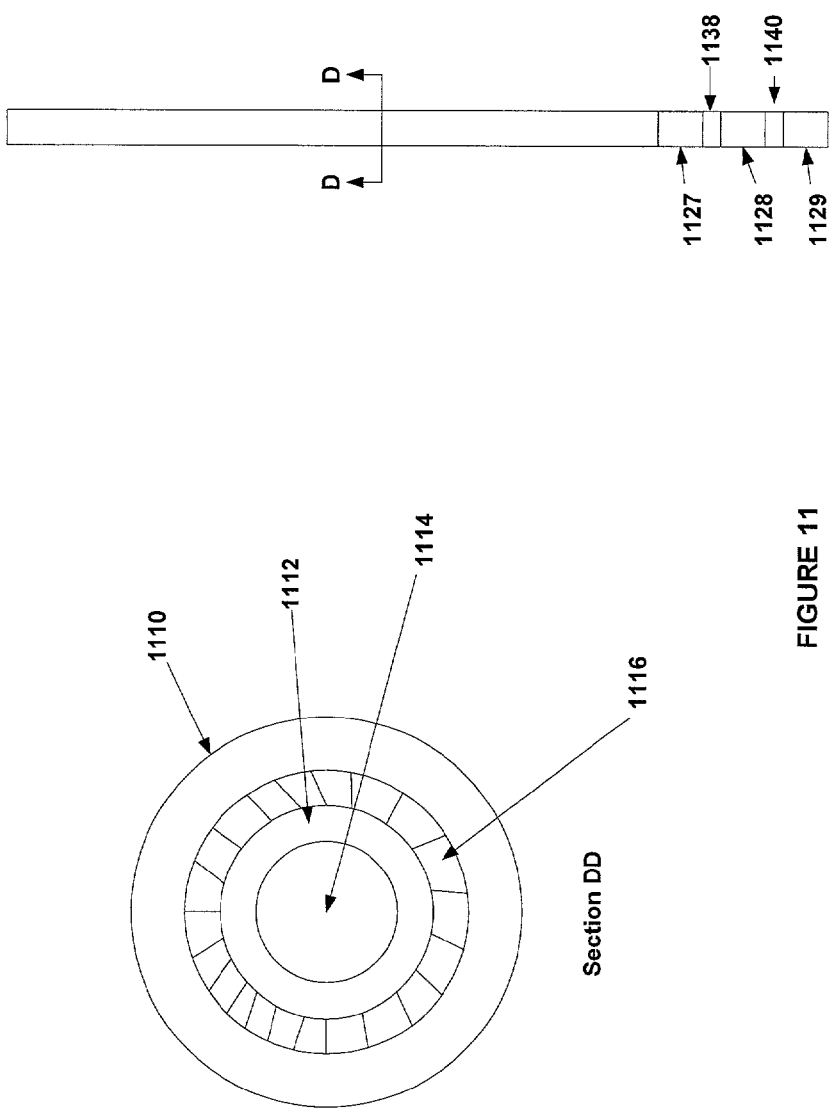
FIG. 11 illustrates an infusion catheter that contains both a lumen and electrodes for use with a combination medical device.

The distal end of catheter 1002 is positioned to deliver desired therapeutic treatment to the targeted sites located in the patient. The targeted sites in the body may vary broadly and may include but are not limited to an internal cavity, a blood vessel, any organ, other tissue or fluid in the body. The distal end of catheter 1002 is further illustrated in FIG. 11, which shows catheter 1002 containing electrodes 1138 and 1140. While this embodiment shows two electrodes, some applications may require a greater or lesser number of electrodes. Each of the electrodes 1138 and 1140 is individually connected to the INS 1205 through a conductor in wire 1116. Cross section DD in FIG. 11 shows wire 1116 in catheter 1002. Catheter 1002 further comprises an outer cylindrical insulation jacket 1110 and an inner cylindrical insulating jacket 1112 that defines a cylindrical catheter lumen 1114.

The combination device may be operated in many different modes enhancing the efficacy of treatment. For example, the implantable drug infusion pump may supply a drug to a targeted site for a specific amount of time followed by stimulation from the neuro stimulator. As an alternative, stimulation might be applied intermittently to a background of continuous or intermittent drug infusion. As one skilled in the art will recognize, the treatment possibilities are further increased with the use of a combination device as compared to any individual device.

Patient directed therapy management will first be described using an INS embodiment shown in FIGS. 3–5. Next, patient directed therapy management will be described using the embodiment of an implantable drug infusion pump shown in FIGS. 7–9. Finally, patient directed therapy management will be described using a combination device embodiment shown in FIGS. 12 and 13.

FIG. 3 generally depicts system components of an embodiment of the present invention that allows a patient to select and access preset patient therapy programs from the INS 5 in preparation for creating personalized therapy programs. The apparatus included are an INS 5 with corresponding leads 15A and 15B, a physician or clinician programmer 40 and a patient programmer 50. In the system apparatus, the clinician programmer 40, the patient programmer 50 and the INS 5 communicate using radio waves, for example via telemetry 3 and 4.

In an embodiment, the clinician programmer 40 is used by the clinician to create preset clinician therapy programs for a particular patient. The clinician can also modify the preset therapy stored in the INS memory 100, troubleshoot the INS 5, and periodically communicate with the INS 5 to manage the patient therapy and collect INS data. The clinician can create the preset clinician therapy programs via the clinician programmer input medium or device 43, for example a keyboard, or any other input component recognized by the clinician programmer controller 45.

The preset clinician therapy programs include specific therapy parameters and electrode settings that can be based on industry or clinician preferences, patient feedback, patient test results, or a combination of all. The clinician can simultaneously view the preset programs as he/she is creating them on the graphical display screen 41. Upon completion of the preset therapy programs, the clinician programmer controller 45 will execute the clinician's instruction to save the preset programs. The clinician programmer controller 45 will save the preset programs in its memory 47 and download a copy to the INS memory 100 via telemetry 3. In an embodiment, only a copy of the preset clinician therapy programs are downloaded to the INS device 5. A master copy of the preset clinician therapy programs remains with the clinician in the clinician programmer memory 47. The stored patient therapy programs (both preset and personalized) in the INS device 5 will allow the INS device 5 to generate the electrical stimulation signals for the patient's specific needs. The therapy programs will control such electrode settings as signal amplitude, rate, pulse width, and directional sequence.

In an embodiment of the present invention, as will be discussed below; a patient can access the preset clinician therapy programs (PCTP) stored in the INS via the patient programmer 50. The patient programmer 50 can comprise a graphical display screen 60, an input medium or device 70, a patient program controller 55, memory 75 and a telemetry block 65. Having accessed a PCTP, the patient can then create at least one personalized therapy program from the accessed PCTP. The patient can then store the new personalized therapy program in the INS 5 via the patient programmer 50 input device 70.

For example, in the embodiment shown in FIG. 3, a patient could step through the following to create and store at least one personalized therapy program 190 (discussed with reference to FIG. 5). First, a patient would turn the patient programmer 50 ON and start the process in a first Start Screen. Second, the patient would select a Review function and interrogate the INS 5 via the input device 70. The patient would then select a Select Menu function that brings up a Selection Screen on the graphical display screen 60. The Selection screen would display a Menu indicating the various preset clinician therapy programs (PCTP) 170 (discussed in more detail with reference to FIG. 5) that are resident in the INS memory 100. The patient could then scroll through the Menu (on the graphical display screen 60) and select the particular PCTP 170 that he/she wishes to access in order to create at least one personalized therapy program. Having accessed a PCTP 170, the patient can then review and modify the preset clinician therapy settings (PCTS) 180 (discussed in more detail with reference to FIG. 5) that correspond to the accessed PCTP 170. The patient may then select and optimize a PCTS 180 as necessary or desired by use of the graphical display screen 60 and the input device 70.

The patient can then make changes as desired for any of the other remaining PCTS 180 of the accessed PCTP 170 as necessary to create a personalized therapy program 190. Once the patient has created a personalized therapy program 190, a Save function can be selected. A Save screen could then be displayed where the user would create a label for the created personalized therapy program. For example, the user could label the just created personalized therapy program 190 a "Sleep" program. The patient would then select a Store function and a Store screen would be displayed. The patient would then, via the input medium key for example, store the personalized therapy program in the INS memory 100. The patient programmer controller 55 will execute the patient's instruction to save the new programs. The patient programmer can save the new programs in its memory 75 and download a copy to the INS memory 100. The new programs will be transmitted via telemetry 4 to the INS 5 where they will be saved in INS memory 100. The patient could repeat the above steps to create other personalized therapy programs 190, for example programs such as "Running", "Eating", "Sitting", "Exercising" and others.

The steps just discussed in creating personalized therapy programs 190 involve patient interaction with the graphical display screen 60 and input device 70 of the patient programmer 50 and can be an embodiment of a personalized therapy algorithm. Those of skill in the art will readily recognize that the patient's commands and instructions are being carried out by the patient programmer controller 55. The controller 55 will then transmit instructions via its telemetry block 65 to the INS 5.

In other embodiments, the patient could create personalized therapy programs as combinations of unmodified preset programs, or combinations of both modified and unmodified preset clinician therapy programs (PCTS) via a similar process.

Having created and stored personalized therapy programs, the patient can then access, modify if necessary, and execute at least one personalized therapy programs via the patient programmer 50. A patient can access the personalized therapy programs via the patient programmer 50. Having accessed the personalized therapy settings, the patient can then optimize and execute the personalized therapy programs to receive therapy.

For example, a patient could step through the following to access and execute at least one personalized therapy program 190. First, a patient would turn the patient programmer 50 ON and start the process in a first Start Screen. Second, the patient would select a Review function and interrogate the INS 5 via the input device 70. The patient would then select a Select Menu function that brings up a Selection Screen on the graphical display screen 60. The Selection screen would display a Menu indicating the various preset clinician therapy programs (PCTP) 170 and personalized therapy programs 190 that are resident in the INS memory 100. The patient could then scroll through the Menu and select the particular personalized therapy program that he/she wishes to access in order to execute for therapy via the INS. Having accessed a personalized therapy program, the patient may then select a personalized therapy program and optimize as necessary or desired by use of the graphical display screen 60 and the input device 70.

If no optimization of the accessed personalized therapy program 190 is done, then an Execute function is selected via the input device 70. An Execute Personalized Therapy Screen will be displayed on the patient programmer display 60. The patient will then select execution of the accessed personalized therapy program 190, for example via the input device 70.

If the patient does optimize the accessed personalized therapy program 190, the Save function would be selected. A Save screen would then be displayed where the user would select a Store function. In a Store screen the patient would then, via the input medium key for example, store the optimized personalized therapy program 190 in the INS device 5. The Execute function is then selected via the input device 70. An Execute Personalized Therapy Screen will be displayed where the patient will select execution of the accessed personalized therapy program 190, for example via the input device 70. Again, the patient programmer controller 55 will carry out the patient's instruction to execute, and optimize if desired, the personalized therapy program 190.

In another embodiment, a patient will be able to execute an automatic timing algorithm on the patient programmer controller 55. The execution of the timing algorithm is similar to the personalized therapy algorithm just discussed. However, while the personalized therapy algorithm allows the patient to create personalized therapy programs and download them to the INS memory 100, the timing algorithm will allow the patient to create personalized automatic sequencing programs where personalized therapy programs, preset therapy programs, or a combination of both will automatically be executed by the INS 5. The patient will store the personalized automatic sequencing programs in the INS memory for subsequent execution at predetermined times for predetermined periods of time. For example, the patient could create a personalized automatic sequencing program that automatically executes certain predetermined therapy programs every morning at 6:30 AM for 1.5 hours.

The INS 5 also uses telemetry 3 and 4 to communicate with the clinician programmer 40 or patient programmer 50. The patient programmer 50 comprises an INS controller 90, memory 100, and a telemetry block 80. The INS controller 90 processes instructions received at the telemetry block 80. In an embodiment, the INS controller 90 will either download or upload data to or from the INS memory 100 depending on the instructions received at the telemetry block 80. The INS memory 100 includes memory sufficient for operation of the INS 5 and storage of all therapy programs. Those skilled in the art will appreciate that the INS memory 100 includes memory such as volatile Random Access Memory (RAM) such as Static RAM, nonvolatile Read Only Memory (ROM), and Electrically Erasable Programmable Read Only Memory (EEPROM) such as Flash EEPROM, as well as other suitable INS memory 100. Once the personalized therapy programs have been downloaded, upon instructions by the patient programmer 50, the INS controller 90 will be able to execute both the preset clinician therapy programs and the personalized therapy programs.

FIG. 4 shows a block diagram depicting a method of the present invention for a patient to create personalized therapy programs for storage in an INS 5. In a first step 110, preset clinician therapy programs with electrode therapy settings are stored in the INS memory 100.

In a second step 120, the patient interactively (as discussed previously with respect to FIG. 3) enters a request, via the patient programmer input medium 70 and graphical display screen 60.

In a third step 130, the preset clinician therapy programs have been accessed and are displayed on the patient programmer graphical display screen 60 and stored in the patient programmer memory 75.

In step four 140, the patient creates personalized therapy programs, with personalized therapy settings (discussed in FIG. 5), by modifying the accessed preset clinician therapy programs. The personalized therapy programs are created through interaction (as discussed previously with respect to FIG. 3) with the patient programmer 50, via the patient programmer input device 70 and graphical display screen 60.

In step five 145, the patient will label the created personalized therapy programs in preparation for saving or storing.

In step six 150, the patient stores the new personalized therapy programs with personalized therapy settings in the INS memory 100, under the particular labels chosen by the patient. Storing is accomplished through interactive manipulation (as discussed previously with respect to FIG. 3) of the patient programmer 50 by the patient. Once the patient requests that the new programs be stored, the patient programmer 50 will download the newly created personalized therapy programs to the INS memory 100, via telemetry communication 4. The INS device 5 will now be able to execute the new stored personalized therapy programs.

In step seven 160, the patient can execute by selecting either a preset clinician therapy program or a personalized therapy program in accordance with the patient's activity and/or preference.

Figure 5:
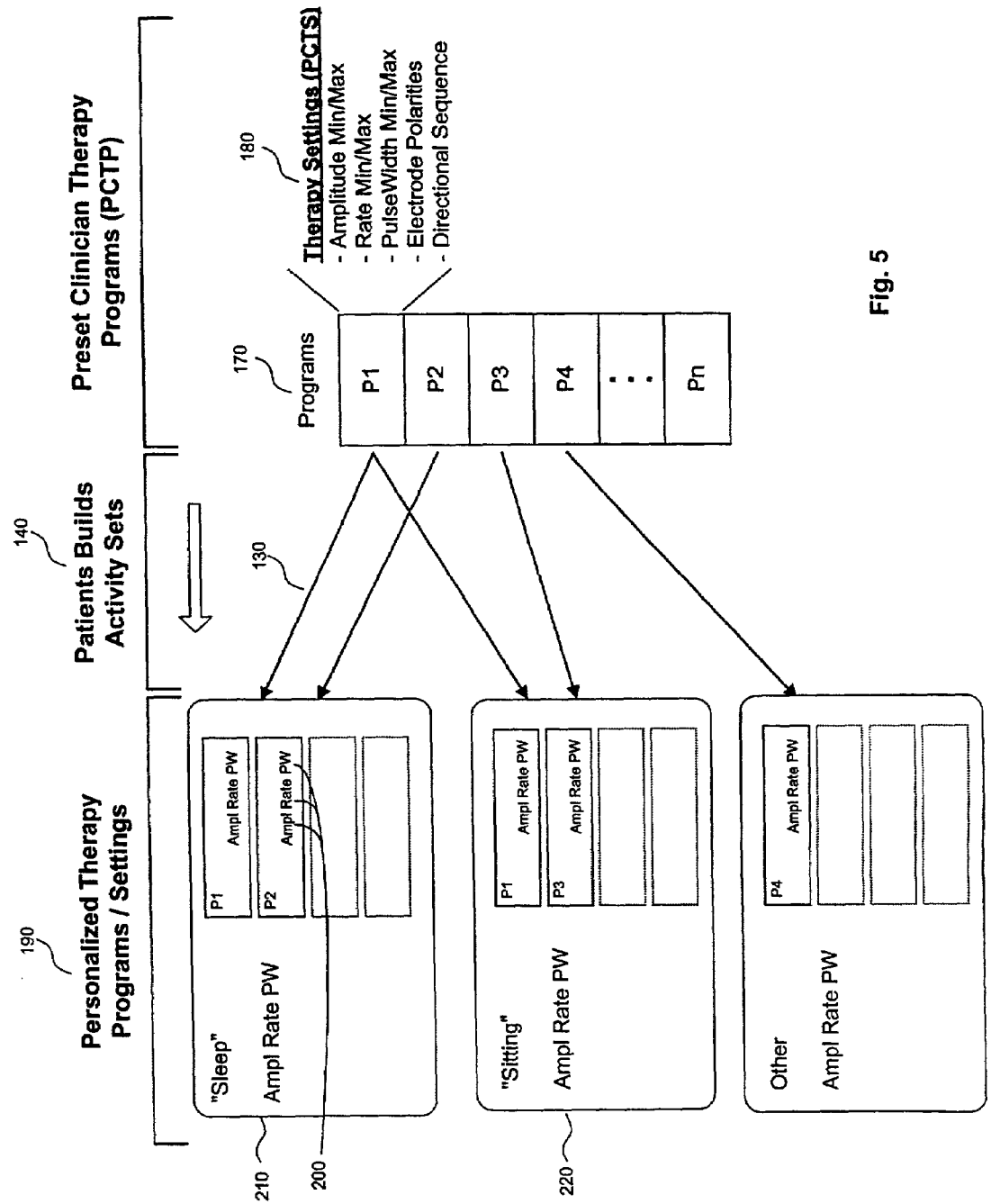
FIG. 5 is a block diagram representation showing in more detail certain steps of FIG. 4 for creating personalized therapy programs.

FIG. 5 depicts a block diagram representation showing, in more detail, steps executed by the patient to create personalized therapy programs from preset therapy programs already present in the INS 5. As discussed previously, physician defined programs or preset clinician therapy programs (PCTP) 170 are created on a clinician programmer 40 (shown in FIG. 3) and downloaded via telemetry 3 and stored (shown in FIG. 3) in the INS memory 100. At the patient's discretion, a patient can access the PCTPs via a patient programmer 70. The patient can then build or create personalized activity sets or personalized therapy programs 190.

Typically, there is more than one PCTP 170 downloaded and stored in the INS memory 100. FIG. 5 shows that there are N number of PCTPs 170 stored in INS memory 100 each labeled P1, P2, P3, P4, . . . PN. Further, each PCTP 170 includes particular Preset Clinician Therapy Setting (PCTS) 180 such as stimulation amplitude, rate, pulse width, electrode polarities, and directional sequence. As a result, each of the PCTPs 170 labeled P1, P2, P3, P4, . . . PN have their own corresponding set of PCTS 180 (Amplitude1, Rate1, PW1; Amplitude2, Rate2, PW2; Amplitude3, Rate3, PW3; . . . AmplitudeN, RateN, PWN). The patient will in turn create his/her own personalized therapy programs 190 with corresponding personalized therapy settings 200 from the available N number of PCTPs 170 stored in the INS memory 100.

The patient, however, has flexibility in creating his/her personalized therapy programs 190 and settings 200. In a first case, the patient can access a single PCTP 170 (e.g., P1) and build or create a personalized therapy program 190 with corresponding personalized settings 200 by adjusting or modifying the PCTS 180 (i.e., Amplitude1, Rate1, PW1) of that single accessed PCTP 170. Having created a personalized therapy program 190, the patient will then define or label the new personalized therapy program 190.

Alternatively, in a second case shown in FIG. 5, the patient can access any two PCTPs 170 (e.g., P1 and P2) to build or create a new personalized therapy program 190. In this case, the patient could decide to make no modifications to the PCTS 180 (i.e. Amplitude1, Rate1, PW1 and Amplitude2, Rate2, PW2) of the chosen PCTPs 170 and simply have this personalized therapy program 190 be a combination of the two chosen PCTPs 170 with their PCTS 180 unmodified. This case is shown by the personalized therapy program 190 labeled "Sleep" 210.

In a third case, as shown in FIG. 5, the patient can access any two PCTPs 170 (e.g., P1 and P3) to build or create a new personalized therapy program 190. In this case, the patient could decide to make changes to the PCTS 180 (i.e., Amplitude1, Rate1, PW1 and Amplitude3, Rate3, PW3) of one or both of the chosen PCTPs 170. The result would be a personalized therapy program 190 that is a combination of the two chosen PCTPs 170 with one or both of the PCTS 180 modified, for example as shown by the personalized therapy program 190 labeled "Sitting" 220. The patient can create any desired number of personalized therapy programs 190 through repetition of the steps discussed with respect to FIGS. 3–5.

Additionally, it will be readily appreciated by those skilled in the art that the patient could actually access any number of PCTPs 170 (i.e., P1, P2, P3 up to PN) or all the PCTPs 170 to build or create a new personalized therapy program 190. In such a case, the patient could make changes to any number or all of the PCTS 180 (i.e., the Amplitude, Rate, PW) of any one or all of the chosen PCTPs 170. The result would then be a personalized therapy program 190 that is a combination of the chosen PCTPs 170 with some or all PCTS 180 modified.

Figure 7:
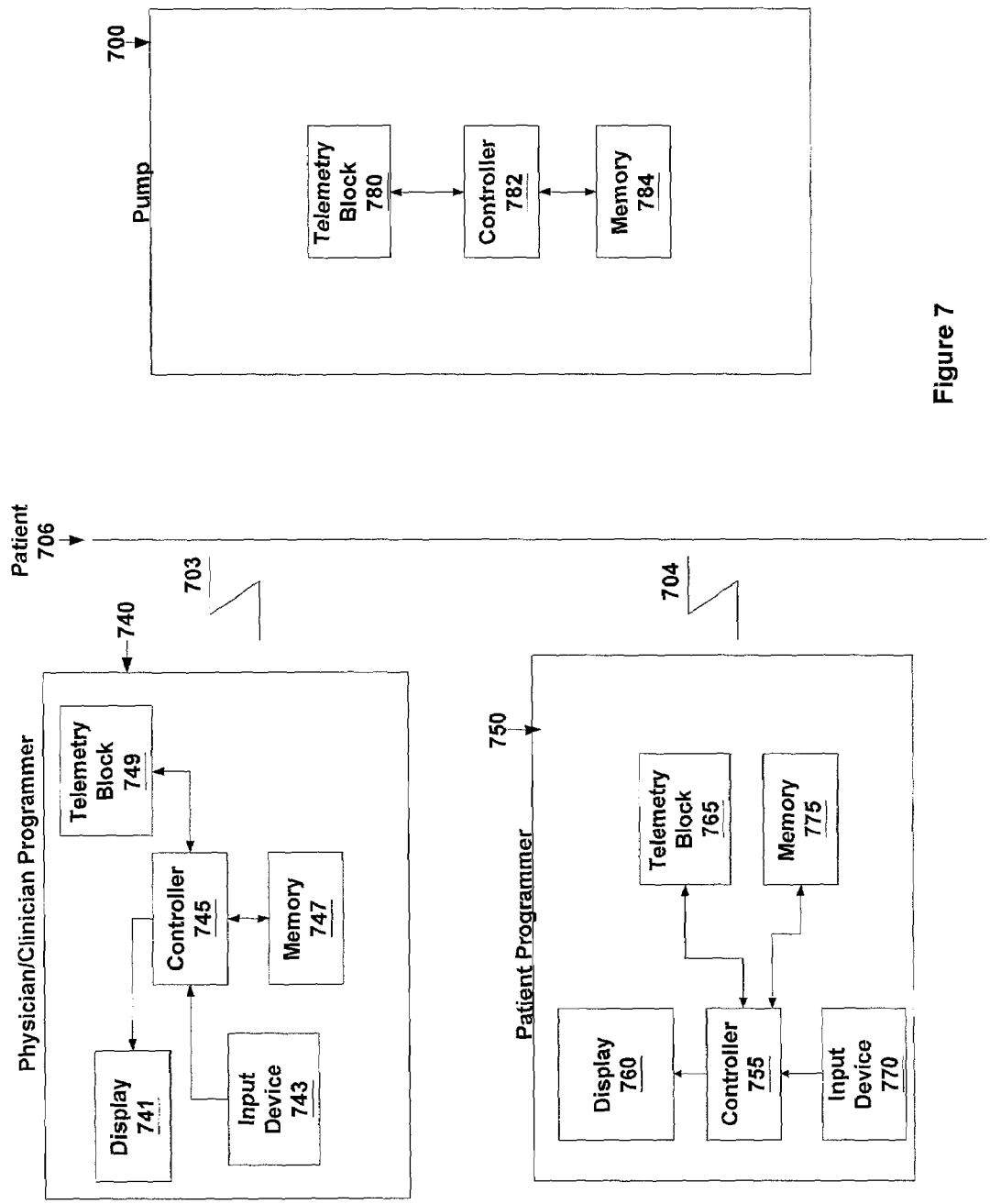
FIG. 7 is a schematic block diagram of an implantable drug infusion pump in accordance with an embodiment of the present invention.

In a second embodiment, the invention is described with the use of an implantable drug infusion pump 700, shown in FIG. 7. FIG. 7 generally depicts system components of an embodiment of the present invention that allows a patient to select and access preset patient therapy programs from the implantable drug infusion pump 700 in preparation for creating personalized therapy programs. The system includes an implantable drug infusion pump 700, a physician or clinician programmer 740, and a patient programmer 750. In the system, the clinician programmer 740, the patient programmer 750, and the implantable drug infusion pump 700 communicate using radio waves, for example via telemetry 703 and 704.

The clinician programmer 740 is used by the clinician to create preset clinician therapy programs for a particular patient. The clinician programmer 740 is similar to the clinician programmer 40, FIG. 3, discussed in the above INS embodiment. Clinician programmers, 740 and 40, contain similar hardware components that perform similar tasks. Such hardware devices may include input device 743, display 741, controller 745, memory 747, and telemetry block 749. Therefore, each of these components will not be discussed in detail. One skilled in the art will recognize that the clinician programmers, 740 and 40, may contain different software because of the different preset clinician therapy programs the clinician programmer may create.

The clinician programmer 740 is used by the clinician to create preset clinician therapy programs for a particular patient. For example, a particular pain patient may have preset bolus programs for the delivery of pain medication beyond a constant basal flow program. The patient could then select the appropriate bolus program based on the severity of breakthrough pain experienced. Another example could be preset programs for insulin delivery to patients with diabetes. The patient could select the appropriate insulin deliver program based upon the size of the meal, or the amount of time they intend to engage in a particular activity such as exercise.

The clinician through the clinician programmer 740 can also modify the preset therapies stored in the implantable drug infusion pump memory 784, troubleshoot the implantable drug infusion pump 700, and periodically communicate with the implantable drug infusion pump 700 to manage the patient therapy and collect implantable drug infusion pump 700 data.

The preset clinician therapy programs include specific therapy parameters that can be based on industry or clinician preferences, patient feedback, patient test results, or a combination of all. Upon completion of the preset therapy programs, the clinician programmer controller 745 will execute the clinician's instruction to save the preset programs. The clinician programmer controller 745 will save the preset programs in its memory 747 and download a copy to the implantable drug infusion pump memory 784 via telemetry 703. A master copy of the preset clinician therapy programs may remain with the clinician in the clinician programmer memory 747. The stored patient therapy programs (both preset and personalized) in the implantable drug infusion device 700 could allow the implantable drug infusion device 700 to establish drug delivery for the patient's specific needs. The therapy programs may control such pump settings as infusion rate, start time, stop time, infusion volume, and drug dosage.

In an embodiment of the present invention, as will be discussed below, a patient can access the preset clinician therapy programs (PCTP) stored in the implantable drug infusion pump via the patient programmer 750. The patient programmer 750 is similar to the patient programmer 50, FIG. 3, discussed in the above INS embodiment. Patient programmers 750 and 50 contain similar hardware components that perform similar tasks. Such hardware devices may include input device 770, display 760, controller 755, memory 775, and telemetry block 765. Therefore, each of these components will not be discussed in detail. One skilled in the art will recognize that the patient programmers 750 and 50 may contain different software because of the different personalized therapy programs the patient programmer may create.

Having accessed a PCTP, the patient can create at least one personalized therapy program from the accessed PCTP. The patient can then store the new personalized therapy program in the implantable drug infusion pump 700 via the patient programmer input device 770.

For example, in the embodiment shown in FIG. 7, a patient could step through the following to create and store at least one personalized therapy program 990 (discussed with reference to FIG. 9). First, a patient would turn the patient programmer 750 ON and start the process in a first Start Screen. Second, the patient would select a review function and interrogate the implantable drug infusion pump 700 via the input device 770. The patient would then select a Select Menu function that brings up a Selection Screen on the graphical display screen 760. The Selection screen would display a Menu indicating the various preset clinician therapy programs (PCTP) 970 (discussed in more detail with reference to FIG. 9) that are resident in the implantable pump memory 784. The patient could then scroll through the Menu (on the graphical display screen 760) and select the particular PCTP 970 that he/she wishes to access in order to create at least one personalized therapy program. Having accessed a PCTP 970, the patient can then review and modify the preset clinician therapy settings (PCTS) 980 (discussed in more detail with reference to FIG. 9) that correspond to the accessed PCTP 970. The patient may then select and optimize a PCTS 980 as necessary or desired by use of the graphical display screen 760 and the input device 770.

The patient can then make changes as desired for any of the other remaining PCTS 980 of the accessed PCTP 970 as necessary to create a personalized therapy program 990. Once the patient has created a personalized therapy program 990, a Save function can be selected. A Save screen could then be displayed where the user would create a label for the created personalized therapy program. For example, the user could label the just created personalized therapy program 990 a "Small Meal" 910 program. The patient would then select a Store function and a Store screen would be displayed. The patient would then, via the input medium key for example, store the personalized therapy program in the implantable drug infusion pump memory 784. The patient could repeat the above steps to create other personalized therapy programs 990, for example programs such as "Medium Meal" 920, "Large Meal" 995, and others.

In other embodiments, the patient could create personalized therapy programs as combinations of unmodified preset programs, or combinations of both modified and unmodified preset clinician therapy programs (PCTS) via a similar process.

Having created and stored personalized therapy programs, the patient can then access, modify if necessary, and execute at least one personalized therapy program via the patient programmer 750. A patient can access the personalized therapy programs via the patient programmer 750. Having accessed the personalized therapy settings, the patient can then optimize and execute the personalized therapy programs to receive therapy. Additionally, a patient could execute an automatic timing algorithm on the patient controller similar to the above timing algorithm described in the INS embodiment.

Figure 8:
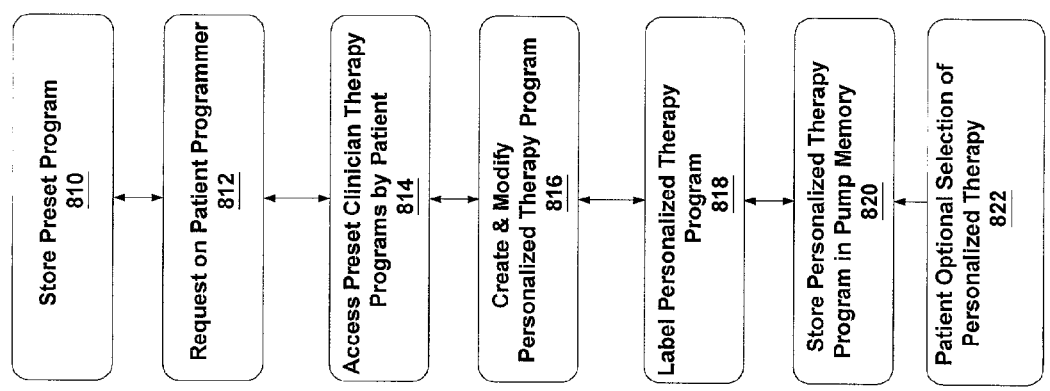
FIG. 8 depicts a block diagram that shows a method of the present invention to create personalized therapy programs.

FIG. 8 shows a block diagram depicting a preferred method of the present invention for a patient to create personalized therapy programs for storage in an implantable drug infusion pump 700. In a first step 810, preset clinician therapy programs with implantable pump settings are stored in the implantable drug infusion pump memory 784

In a second step 812, the patient interactively enters a request, via the patient programmer input medium 770 and graphical display screen 760. In a third step 814, the preset clinician therapy programs have been accessed and are displayed on the patient programmer graphical display screen 760 and stored in the patient programmer memory 775.

In step four 816, the patient creates personalized therapy programs, with personalized therapy settings, by modifying the accessed preset clinician therapy programs. The personalized therapy programs are created through interaction with the patient programmer 750, via the patient programmer input device 770, and graphical display screen 760. In step five 818, the patient could label the created personalized therapy programs in preparation for saving or storing.

In step six 820, the patient stores the new personalized therapy programs with personalized therapy settings in the implantable drug infusion pump memory 784, under the particular labels chosen by the patient. Finally, in step seven 822, the patient can execute by selecting either a preset clinician therapy program or a personalized therapy program in accordance with the patient's activity and/or preference.

Figure 9:
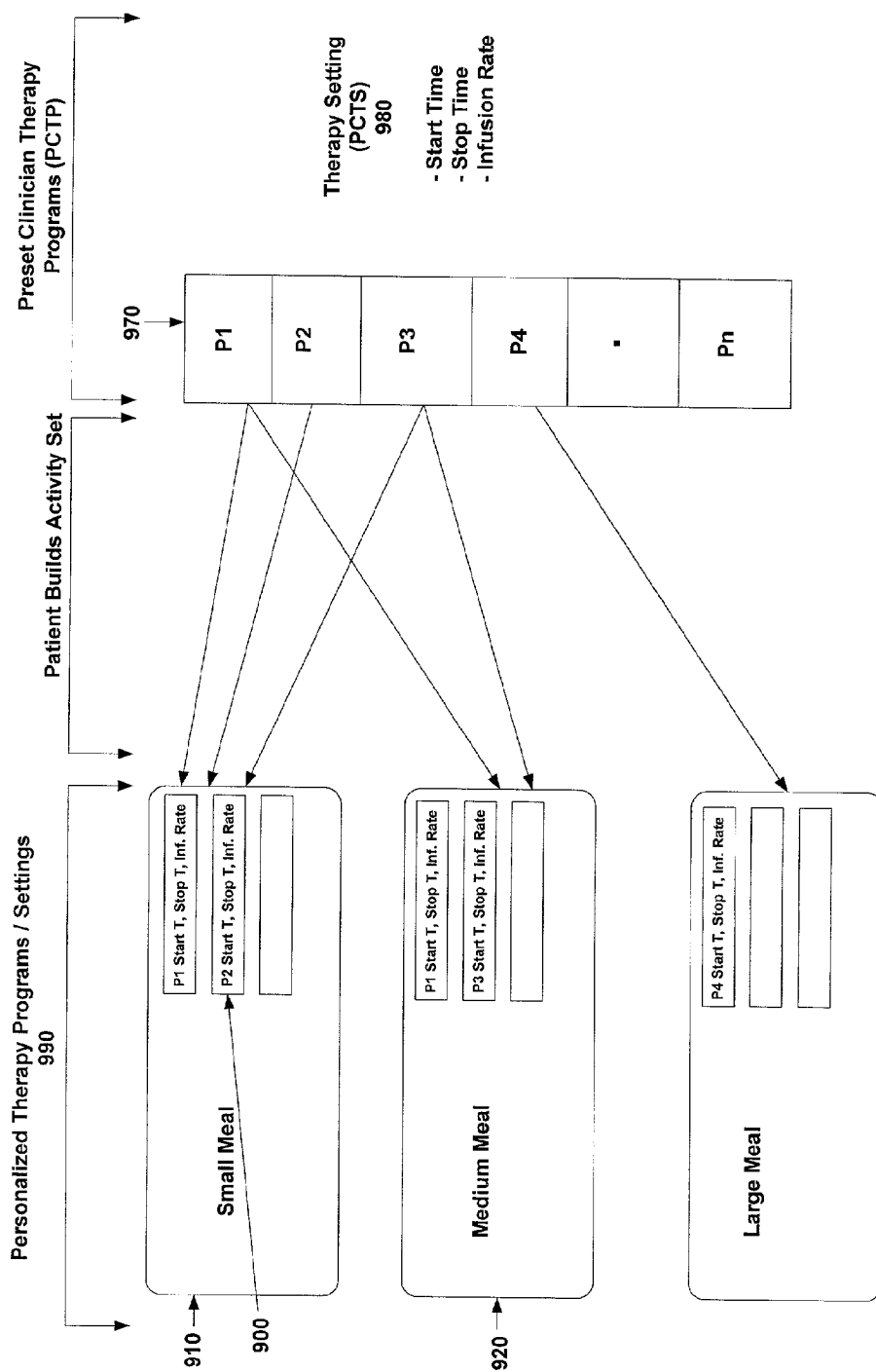
FIG. 9 is a block diagram representation showing in more detail certain steps of FIG. 8 for creating personalized therapy programs.

FIG. 9 depicts a block diagram representation showing, in more detail, steps executed by the patient to create personalized therapy programs from preset therapy programs already present in the implantable drug infusion pump 700. As discussed previously, physician defined programs or preset clinician therapy programs (PCTP) 970 are created on a clinician programmer 740 (shown in FIG. 7) and downloaded via telemetry 703 and stored (shown in FIG. 7) in the implantable drug infusion memory 784. At the patient's discretion, a patient can access the PCTPs via a patient programmer 750. The patient can then build or create personalized activity sets or personalized therapy programs 990.

Typically, there is more than one PCTP 970 downloaded and stored in the implantable drug infusion pump memory 784. FIG. 9 shows that there are N number of PCTPs 970 stored in implantable drug infusion pump memory 784 each labeled P1, P2, P3, P4, . . . PN. Further, each PCTP 970, includes particular preset clinician therapy setting (PCTS) 980 such as start time, stop time and infusion rate. As a result, each of the PCTPs 970 labeled P1, P2, P3, P4, . . . PN have their own corresponding set of PCTS 980 (Start Time1, Stop Time1, Infusion Rate 1; Start Time2, Stop Time2, Infusion Rate2; Start Time3, Stop Time3, Infusion Rate3; . . . Start TimeN, Stop TimeN, Infusion RateN). The patient will in turn create his/her own personalized therapy programs 990 with corresponding personalized therapy settings 900 from the available N number of PCTPs 970 stored in the implantable pump memory 784.

The patient, however, has flexibility in creating his/her personalized therapy programs 990 and settings 900. In a first case, the patient can access a single PCTP 970 (e.g., P1) and build or create a personalized therapy program 990 with corresponding personalized settings 900 by adjusting or modifying the PCTS 980 (i.e., Start Time1, Stop Time1, Infusion Rate1) of that single accessed PCTP 970. Having created a personalized therapy program 990, the patient will then define or label the new personalized therapy program 990.

Alternatively, in a second case shown in FIG. 9, the patient can access any two PCTPs 970 (e.g., P1 and P2) to build or create a new personalized therapy program 990. In this case, the patient could decide to make no modifications to the PCTS 980 (i.e. ., Start Time1, Stop Time1, Infusion Rate1 and Start Time2, Stop Time2, Infusion Rate2) of the chosen PCTPs 970 and simply have this personalized therapy program 990 be a combination of the two chosen PCTPs 970 with their PCTS 980 unmodified. This case is shown by the personalized therapy program 990 labeled "Small Meal" 910.

In a third case, as shown in FIG. 9, the patient can access any two PCTPs 970 (e.g., P1 and P3) to build or create a new personalized therapy program 990. In this case, the patient could decide to make changes to the PCTS 980 (i.e., Start Time1, Stop Time1, Infusion Rate1 and Start Time3, Stop Time3, Infusion Rate3) of one or both of the chosen PCTPs 970. The result would be a personalized therapy program 990 that is a combination of the two chosen PCTPs 970 with one or both of the PCTS 980 modified, for example as shown by the personalized therapy program 990 labeled "Medium Meal" 920. The patient can create any desired number of personalized therapy programs 990 through repetition of the steps discussed with respect to FIGS. 7–9.

Additionally, it will be readily appreciated by those skilled in the art that the patient could actually access any number of PCTPs 970 (i.e., P1, P2, P3 up to PN) or all the PCTPs 970 to build or create a new personalized therapy program 990. In such a case, the patient could make changes to any number or all of the PCTS 980 (i.e., Start Time, Stop Time, Infusion Rate, Drug Dosage) of any one or all of the chosen PCTPs 970. The result would then be a personalized therapy program 990 that is a combination of the chosen PCTPs 970 with some or all PCTS 980 modified.

Figure 12:
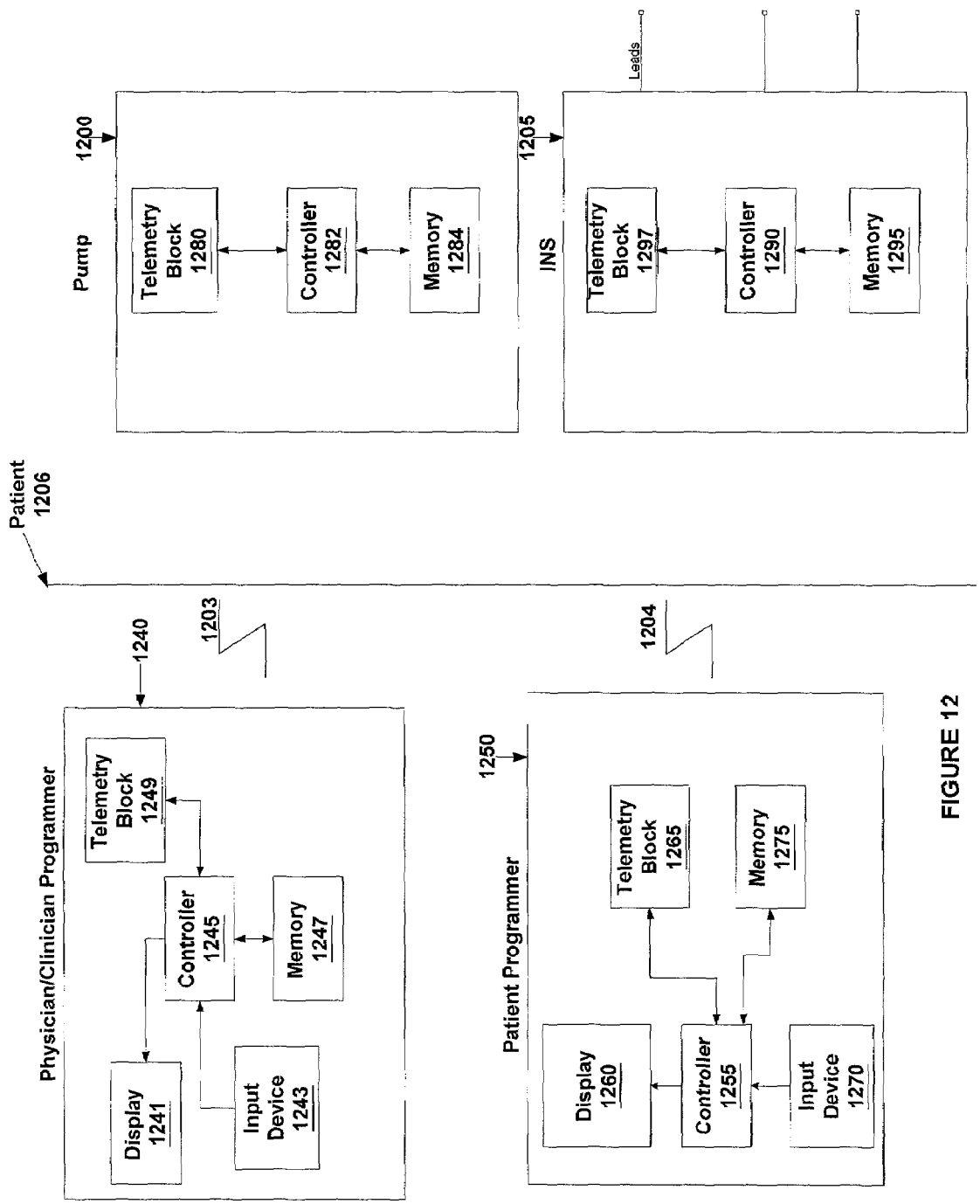
FIG. 12 is a schematic block diagram of a combination implantable drug infusion pump and neuro stimulator in accordance with an embodiment of the present invention.

In a third embodiment, the invention is described with the use of a combination device comprising an implantable drug infusion pump 1200 and an INS 1205, as illustrated in FIG. 12. In other embodiments, the combination device may comprise a number of different devices that increase effectiveness of a patient's therapy. Other devices may include but are not limited to pacemakers, defibrillators, cochlear implants, and other implantable medical treatment devices for the delivery of medical treatments to a patient's body.

FIG. 12 generally depicts system components of an embodiment of the present invention that allows a patient to select and access preset patient therapy programs from a combination device comprising both an implantable drug infusion pump 1200 and an INS 1205 in preparation for creating personalized therapy programs. The system includes an implantable drug infusion pump 1200, an INS 1205 with electrodes, a physician or clinician programmer 1240, and a patient programmer 1250. In the system, the clinician programmer 1240, the patient programmer 1250, the implantable drug infusion pump 1200, and the INS 1205 communicate using radio waves, for example via telemetry 1203 and 1204.

The clinician programmer 1240 is similar to the clinician programmers 40 and 740, described above. All of these clinician programmers contain similar hardware components that perform similar tasks. Such hardware components may include input device 1243, display 1241, controller 1245, memory 1247, and telemetry block 1249. Therefore, each of these components will not be discussed in detail. One skilled in the art will recognize that the clinician programmers, 40, 740 and 1240, may contain different software because of the different preset clinician therapy programs the clinician programmer may create.

A patient can access the preset clinician therapy programs (PCTP) stored in the combination device via the patient programmer 1250. The patient programmer 1250 is similar to the patient programmer 50 and 750 discussed above. All of these patient programmers contain similar hardware components that perform similar tasks. Such hardware devices may include input device 1270, display 1260, controller 1255, memory 1275, and telemetry block 1265. Therefore, each of these components will not be discussed in detail. One skilled in the art will recognize that the patient programmers 50, 750, and 1250 may contain different software because of the different personalized therapy programs the patient programmers may create.

Having accessed a PCTP, a patient can create at least one personalized therapy program from the accessed PCTP. The patient can then store the new personalized therapy program in the combination device via the patient programmer 1250. The procedure for a patient to create and store at least one personalized program is similar to the procedure discussed in both the implantable drug infusion pump and INS embodiments discussed above.

The method of the present invention for a patient to create personalized therapy programs in a combination device is similar to the block diagrams showing the method for INS embodiment, FIG. 4, or the implantable drug infusion pump embodiment, FIG. 8. First, at least one preset therapy program is accessed from the combination device memory. The preset clinician therapy programs that are accessed are displayed on the patient programmer and stored in the patient programmer memory. Next, the patient creates personalized therapy programs, with personalized therapy settings, by modifying the accessed preset clinician therapy programs. Subsequently, the patient may label the created therapy programs in preparation for saving or storing. Finally, the patient can execute the new personalized therapy programs.

Having created and stored personalized therapy programs, the patient can then access, modify if necessary, and execute at least one personalized therapy program via the patient programmer 1250. A patient can access the personalized therapy programs via the patient programmer 1250. Having accessed the personalized therapy settings, the patient can then optimize and execute the personalized therapy programs to receive therapy. Additionally, a patient will be able to execute an automatic timing algorithm on the patient controller similar to the above timing algorithm described in the INS embodiment.

Figure 13:
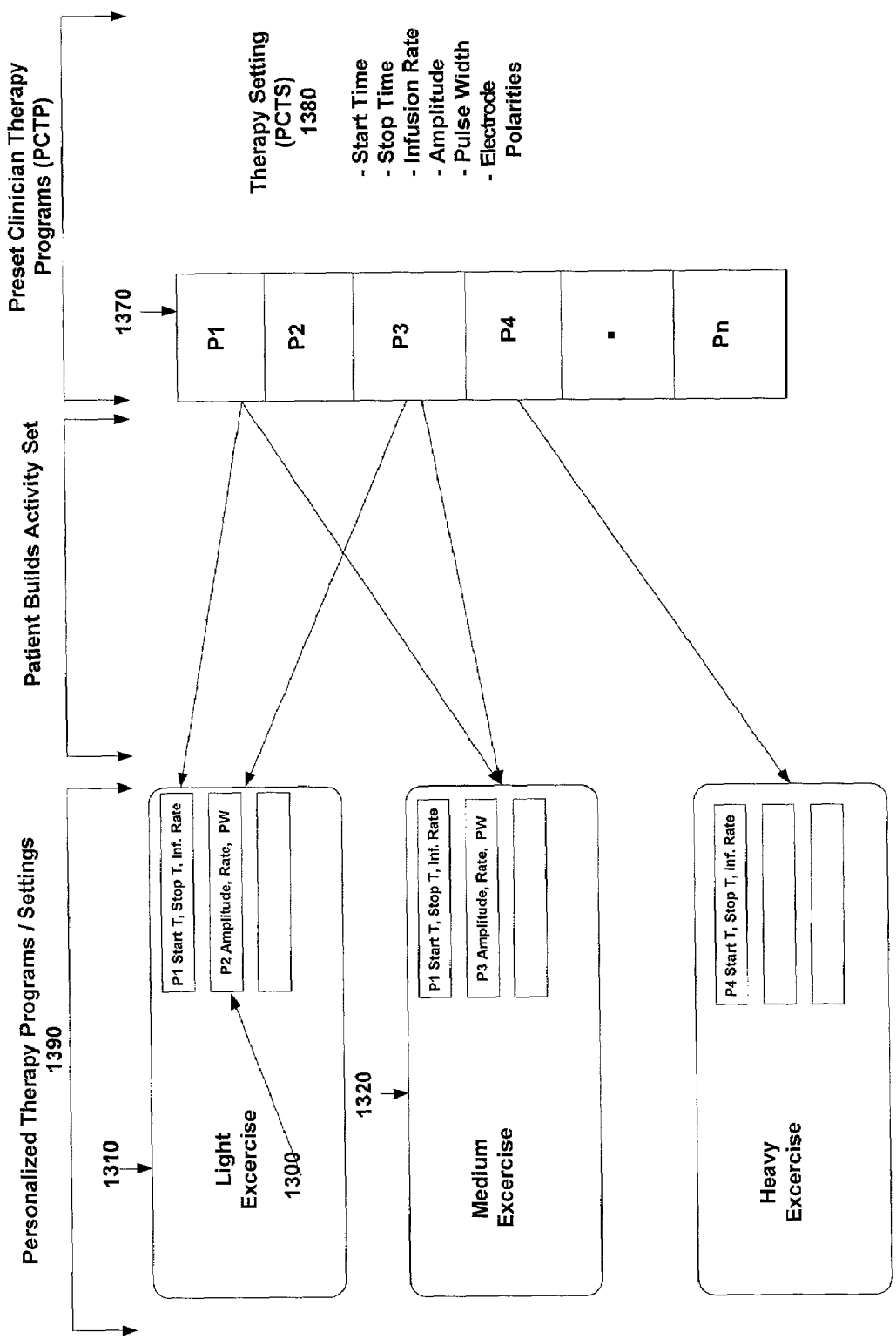
FIG. 13 is a block diagram illustrating a method of creating a personalized therapy program for a combination device.

FIG. 13 depicts a block diagram representation showing, in more detail, steps executed by the patient to create personalized therapy programs from preset therapy programs already present in a combination device. Physician defined programs or preset clinician therapy programs (PCTP) 1370 are created on a clinician programmer 1240 (shown in FIG. 12) and downloaded via telemetry 1203 and stored (shown in FIG. 12) in the combination device memory 1284 and/or 1295. At the patient's discretion, a patient can access the PCTPs via a patient programmer 1250. The patient can then build or create personalized activity sets or personalized therapy programs 1390.

Typically, there is more than one PCTP 1370 downloaded and stored in a combination device memory 1284 and/or 1295. FIG. 13 shows that there are N number of PCTPs 1370 stored in combination device memory 1284 and/or 1295 each labeled P1, P2, P3, P4, . . . PN. Further, each PCTP 1370, may include particular preset clinician therapy setting (PCTS) 1380 such as start time, stop time, infusion rate, amplitude, and pulse width. As a result, each of the PCTPs 1370 labeled P1, P2, P3, P4, . . . PN have their own corresponding set of PCTS 1380 (Start Time1, Stop Time1, Infusion Rate 1; Amplitude2, Rate2, PW2; Amplitude3, Rate3, PW33; . . . Start TimeN, Stop TimeN, Infusion RateN). The patient will in turn create his/her own personalized therapy programs 1390 with corresponding personalized therapy settings 1300 from the available N number of PCTPs 1370 stored in the combination device memory 1284 and/or 1295.

The patient, however, has flexibility in creating his/her personalized therapy programs 1390 and settings 1300. In a first case, the patient can access a single PCTP 1370 (e.g., P1) and build or create a personalized therapy program 1390 with corresponding personalized settings 1300 by adjusting or modifying the PCTS 1380 (i.e., Start Time1, Stop Time1, Infusion Rate1) of that single accessed PCTP 1370. Having created a personalized therapy program 1390, the patient will then define or label the new personalized therapy program 1390.

Alternatively, in a second case shown in FIG. 13, the patient can access any two PCTPs 1370 (e.g., P1 and P2) to build or create a new personalized therapy program 1390. In this case, the patient could decide to make no modifications to the PCTS 1380 (i.e., Start Time1, Stop Time1, Infusion Rate1 and Amplitude2, Rate2, PW2) of the chosen PCTPs 1370 and simply have this personalized therapy program 1390 be a combination of the two chosen PCTPs 1370 with their PCTS 1380 unmodified. This case is shown by the personalized therapy program 1390 labeled "Light Exercise" 1310.

In a third case, as shown in FIG. 13, the patient can access any two PCTPs 1370 (e.g., P1 and P3) to build or create a new personalized therapy program 1390. In this case, the patient could decide to make changes to the PCTS 1380 (i.e., Start Time1, Stop Time1, Infusion Rate1 and Amplitude3, Rate3, PW3) of one or both of the chosen PCTPs 1370. The result would be a personalized therapy program 1390 that is a combination of the two chosen PCTPs 1370 with one or both of the PCTS 1380 modified, for example as shown by the personalized therapy program 1390 labeled "Medium Exercise" 1320. The patient can create any desired number of personalized therapy programs 1390 through repetition of the steps discussed with respect to FIGS. 12–13.

Additionally, it will be readily appreciated by those skilled in the art that the patient could actually access any number of PCTPs 1370 (i.e., P1, P2, P3 up to PN) or all the PCTPs 1370 to build or create a new personalized therapy program 1390. In such a case, the patient could make changes to any number or all of the PCTS 1380 (i.e., Start Time, Stop Time, Infusion Rate, Drug Dosage) of any one or all of the chosen PCTPs 1370. The result would then be a personalized therapy program 1390 that is a combination of the chosen PCTPs 1370 with some or all PCTS 1380 modified.

The embodiments of the present invention have discussed how a patient is able to access and create personalized therapy programs through the interactive operation of a patient programmer. However, those skilled in the art will recognize that a patient programmer is only one of many components that can be used for this function. For example, a computing device could also be used as the medium to create and store personalized therapy programs.

Additionally, it will be apparent to those skilled in the art that the arrangement and configuration of the components discussed above represent only a few of the possible embodiments of the present invention. For example, those skilled in the art will recognize that the present invention can also be used with an External Neuro Stimulator (not shown), an External Drug Infusion Pump (not shown), and an External Combination Device (not shown) with a catheter implanted into a patient percutaneously, a physician programmer, and a patient programmer. The external devices would function similarly to the implantable devices but are not designed for implantation.

Those skilled in that art will recognize that the discussed embodiments may be altered or amended without departing from the true spirit and scope of the invention. Thus, while various alteration and permutations are possible, the invention is limited only by the following claims and equivalents.

We claim:

1. A method for patient directed therapy management for a drug delivery pump, the method comprising the steps of:
   a) accessing by a patient at least two preset clinician drug therapy programs stored in the drug delivery pump;
   b) modifying the accessed at least two preset clinician drug therapy programs by the patient;
   c) creating at least one personalized drug therapy program by the patient from the modified at least two preset clinician drug therapy programs, the at least one personalized drug therapy program based on patient activity; and
   d) executing at least one personalized drug therapy program for the drug delivery pump.

2. The method for patient directed therapy management of claim 1, wherein the personalized drug therapy program comprises at least one personalized therapy setting.

3. The method for patient directed therapy management of claim 2, wherein the personalized therapy setting comprises an infusion rate.

4. The method for patient directed therapy management of claim 2, wherein the personalized therapy setting comprises a start time.

5. The method for patient directed therapy management of claim 2, wherein the personalized therapy setting comprises a stop time.

6. The method for patient directed therapy management of claim 2, wherein the personalized therapy setting comprises an infusion volume or drug dose.

7. The method for patient directed therapy management of claim 1, wherein the drug delivery pump comprises an implantable pump.

8. The method for patient directed therapy management of claim 1, wherein the drug delivery pump comprises an external pump.

9. The method for patient directed therapy management of claim 1 further comprising the step of storing the personalized drug therapy program in the drug delivery pump.

10. The method for patient directed therapy management of claim 1, wherein a patient programmer is used to communicate with the drug delivery pump.

11. The method for patient directed therapy management of claim 10, wherein the drug delivery pump and the patient programmer communicate via telemetry.

* * * * *